United States Patent
Thomson et al.

(10) Patent No.: US 11,513,056 B2
(45) Date of Patent: Nov. 29, 2022

(54) PARALLEL SINGLE CELL LENS FREE OPTICAL DIELECTROPHORESIS CYTOMETER

(71) Applicant: University of Manitoba, Winnipeg (CA)

(72) Inventors: Douglas Thomson, Winnipeg (CA); Gregory Bridges, Winnipeg (CA); Elham Salimi, Winnipeg (CA); Azita Fazelkhah, Winnipeg (CA); Samaneh Afshar Delkhah, Montreal (CA); Nicholas Durham, Vancouver (CA)

(73) Assignee: University of Manitoba, Winnipeg (CA)

( * ) Notice: Subject to any disclaimer, the term of this patent is extended or adjusted under 35 U.S.C. 154(b) by 0 days.

(21) Appl. No.: 17/061,684

(22) Filed: Oct. 2, 2020

(65) Prior Publication Data
US 2021/0140871 A1    May 13, 2021

Related U.S. Application Data

(60) Provisional application No. 62/910,170, filed on Oct. 3, 2019.

(51) Int. Cl.
*G01N 15/14* (2006.01)
*G01N 33/49* (2006.01)
*G01N 15/00* (2006.01)
*G01N 15/10* (2006.01)

(52) U.S. Cl.
CPC ......... *G01N 15/1436* (2013.01); *G01N 33/49* (2013.01); *G01N 2015/035* (2013.01); *G01N 2015/1006* (2013.01)

(58) Field of Classification Search
CPC ............... G01N 15/1436; G01N 33/49; G01N 2015/035; G01N 2015/1006; G01N 15/1429; G01N 15/1425; G01N 15/1459; G01N 15/1434; G01N 15/14
USPC ...................................................... 356/369
See application file for complete search history.

(56) References Cited

U.S. PATENT DOCUMENTS

2007/0086918 A1* 4/2007 Hartley .............. G01N 15/1484 422/73
2019/0054466 A1* 2/2019 Gershtein .......... G01N 15/1436

* cited by examiner

*Primary Examiner* — Roy M Punnoose
(74) *Attorney, Agent, or Firm* — Kyle R Satterthwaite; Ryan W Dupuis; Ade & Company Inc.

(57) ABSTRACT

A dual light source lens-free dielectrophoresis (DEP) flow cytometer for massively parallel single cell analysis. Each cells dielectric is inferred from measuring their altitude and subsequently velocity change due to DEP actuation in a microfluidic channel. Dual LED sources facilitate velocity measurement by producing two shadows for each cell passing through the channel. These shadows are detected using a linear optical array detector. Massively parallel analysis is possible as each pixel of the detector can independently analyze the passing cells. The DEP cytometer is composed of simple modular components and has the potential to be scaled to achieve a significantly high throughput label-free single-cell analyzer.

14 Claims, 7 Drawing Sheets

PARALLEL SINGLE CELL LENS FREE OPTICAL DIELECTROPHORESIS CYTOMETER

CROSS-REFERENCE TO RELATED APPLICATIONS

This application claims benefit under 35 U.S.C. 119(e) of U.S. Provisional Application No. 62/910,170, filed Oct. 3, 2019, the entirety of which is incorporated herein by reference.

FIELD OF THE INVENTION

The present invention relates to dielectrophoresis cytometers.

BACKGROUND

Dielectrophoresis (DEP) has proven to be a useful technique for single cell analysis. A number of physiological changes produce significant dielectric changes in cells. Under the appropriate conditions, DEP analysis can measure changes in either the cytoplasm or the cell membrane. DEP has been applied to the identification of different cell types in blood analysis [1-3], single cell manipulation [4], identification and isolation of circulating tumor cells [5-7], differentiation of cancerous cells from healthy ones [8,9], identification of different types of cultured tumor cells [3,10], characterization of biological cells [11,12], characterization of the breast cancer cells [13], stem cell differentiation and separation [14-17], tracking apoptosis and monitoring the effects of nutrient deprivation [18-21]. For example, apoptosis dramatically changes ion concentrations in the cytoplasm as well as the effective surface area of the cell membrane and consequently its cytoplasm conductivity and membrane capacitance [19,21-27]. DEP has the advantage of being label free compared to techniques such as flow cytometry and magnetic bead attachment technologies. Cytometry and magnetic bead attachment are powerful for cell characterization and separation, but require cells to be incubated with dyes or magnetic beads [25-27]. Other label-free dielectric based methods exist for single cell analysis, including impedance-based analysis and electrorotation. Impedance-based analysis methods use electrodes within the channel to measure the impedance perturbation due to passing cells [31-35]. Impedance-based analysis can have throughput exceeding 100 cells/s but requires corrections for background media dielectric properties in order the extract quantitative estimates of cell dielectric properties and to enhance signals uses small channels that are prone to clogging. Electrorotation is also a single cell approach however; the throughput of this method is in the one cell per minute range [36-39].

Dielectrophoresis analysis uses the movement of cells from forces generated in electric field gradients to deduce dielectric properties [40]. DEP analysis methods use many different approaches to detect the magnitude and sign of the forces acting on the cells. One of the earliest methods used was the direct observation of the movement of cells in the neighborhood of high field gradients under a microscope [41]. This method is still used by many researchers as apparatus is relatively accessible. Although this is an effective analysis tool; it is highly manual, low throughput and not easily automated. There are also number of approaches that use DEP trapping to infer dielectric properties [26,42-44]. There are DEP trapping based systems to measure dielectrophoretic collection rate (DCR) [9; 41]. This approach relates the dielectric properties of the cells to the number of the cells accumulated on the electrode pin or edge as they flow over it and the polarizability expression is scaled by a phenomenological factor. These methods do not provide an accurate measurement of cell polarizability. Moreover, there is a need for a microscope, video camera and complex image analysis. Trapping based DEP systems have the advantage of being scalable and have been demonstrated in CMOS technology [44]. However, trapping is a slow process and also exposes the cells to electric field magnitudes that could alter the cell via processes such as electroporation and in many cases are limited to positive DEP [45]. A number of methods make use of dielectrophoresis movement of cells within a flow channel. Microwave interferometers have been used for differential dielectrophoresis flow cytometers and are able to reproducibly measure small changes in dielectric properties [20,46]. However, this approach is difficult to scale to a large number of independent channels. CMOS based DEP cytometers have been reported suitable for use up to one cell per second and have the potential to scale to a large number of parallel channels [47]. However, CMOS systems would have significant initial development costs. Dielectrophoresis-field-flow fractionation (DEP-FFF) is a method that has proven very useful for the analysis of cells. It can analyze relatively large numbers of cells, but analyzes cells that are pulsed into a channel and then measures the elution time of the pulse of cells through a relatively long channel [2,7,48,49]. Recently particle imaging velocimetry (Ply) has been used to perform DEP analysis of cells. However, this approach makes use of very costly image acquisition and analysis equipment [50]. There are also insulator based DEP or iDEP approaches that make use of field gradients created around insulating objects placed within channels [51-54]. The iDEP approaches also use microscopes and require image analysis. The extraction of quantitative dielectric properties from the images taken as the cells flow past these objects is challenging. The balance of dielectric forces over electrodes skewed to the channel and fluid flow forces has also been used to create a dielectric spring that can be used to extract dielectric properties of cells [55]. This approach is continuous and fast enough to measure populations on a cell-by-cell basis, and is automated. However, the throughput of this approach is 4 cells per second [55].

Accordingly, there remains room for improved and alternative solutions for dielectrophoretic cytometry.

SUMMARY OF THE INVENTION

According to one aspect of the invention, there is provided a lens-free dielectrophoretic cytometer comprising:
a fluid channel;
an inlet port arranged for admission of fluid into said fluid channel for flow therethrough in a longitudinal direction thereof;
a linear photodiode array lying cross-wise to said fluid channel in the width direction thereof at a spaced distance downstream from the inlet port;
situated oppositely above and below the fluid channel:
   a pair of cooperating electrodes also lying cross-wise to said fluid channel in the width direction thereof at a location situated downstream from the inlet port, and in upstream adjacency to the photodiode array; and a pair of light emitters positioned in longitudinally spaced apart relation from one another to cast light onto the photodiode array at different angles of incidence.

According to another aspect of the invention, there is provided a method of performing dielectrophoretic cytometry, said method comprising:

(a) causing flow of a fluid sample on a flow path that passes between (i) a linear photodiode array that lies cross-wise to said flow path, and (ii) a pair of light emitters that are spaced apart along said flow path to cast light on said linear photodiode array at different angles of incidence; and (b) during the flow of said fluid sample along said flow path, and during both a deenergized-measurement period characterized by absence of any applied electric field to the flowing fluid, and an energized-measurement period characterized by application of an electric field to the flowing fluid, detecting from each pixel of the photodiode array pairs of sequentially adjacent minima in an output signal of said pixel, wherein each detected pair of sequentially adjacent minima comprises a first minimum denoting passage of a particle between said pixel of the photodiode array and a first one of the light emitters, and a second minimum denoting passage of said particle between the said pixel of the photodiode array and a second one of the light emitters.

Disclosed embodiments present a dual source lens-free optical system for label-free high throughput DEP analysis of single cells. In preferred embodiment, two light emitting diodes (LEDs), a linear CMOS optical detector array, and two co-planar electrodes are used to create a lens-free optical DEP cytometer. Lens-free optical cytometers have the advantage of simple optics, but conventionally use 2-dimensional array detectors. Using a linear optical detector array with dual light sources, massively parallel analysis is possible, as each detector pixel can be used to independently measure the velocity of a passing particle, whereby analysis of more than one particle per second may be achieved.

BRIEF DESCRIPTION OF THE DRAWINGS

One preferred embodiment of the invention will now be described in conjunction with the accompanying drawings in which.

DETAILED DESCRIPTION

Figure 1A:
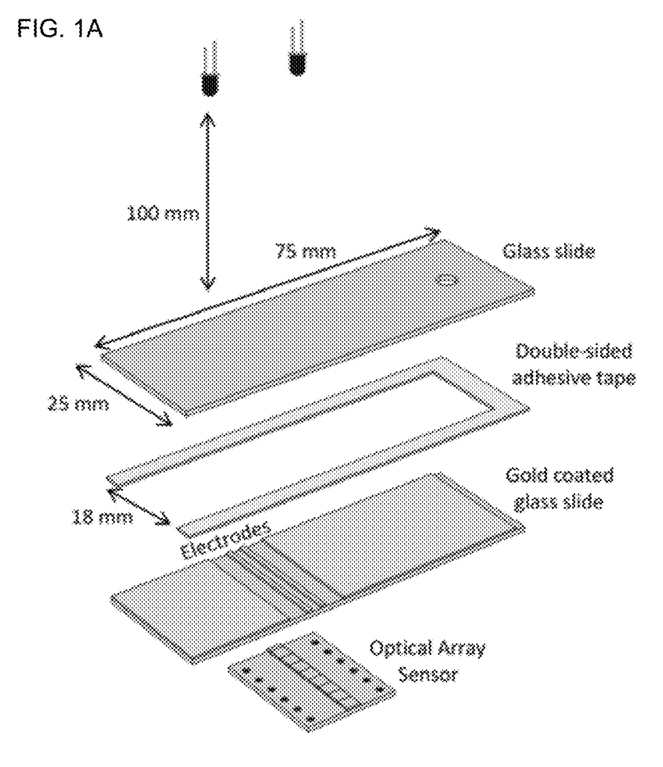
FIG. 1A shows an exploded schematic diagram of an optical DEP cytometer sensor with two light sources, optical detector and microfluidic channel.
Figure 1B:
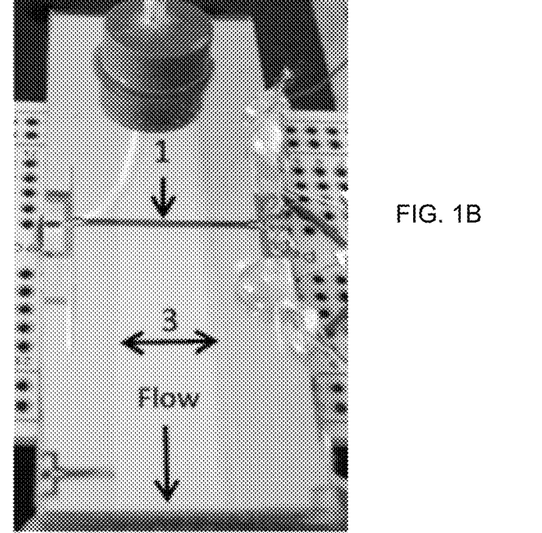
FIG. 1B shows an assembled optical DEP cytometer sensor including electrodes (1) and microfluidic channel (3) mounted together.
Figure 1C:
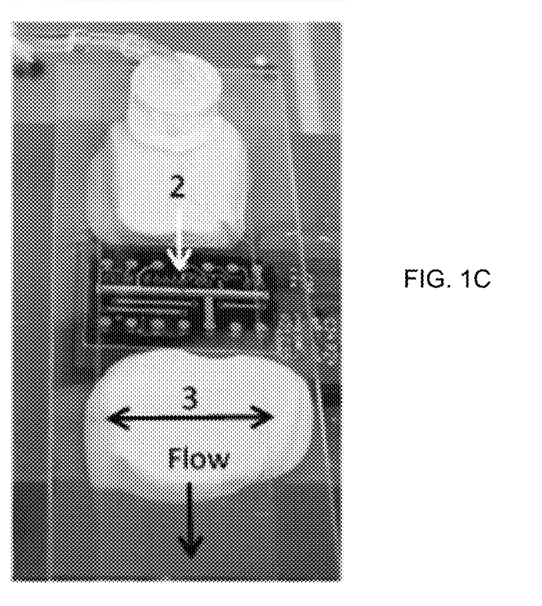
FIG. 1C shows the sensor of FIG. 1B with gold plating on a bottom slide of the sensor omitted to visually reveal the optical detector (2).

FIG. 1 illustrates a preferred embodiment of the present invention, in which two light emitters (e.g. light emitting diodes (LEDs)), a linear CMOS optical detector array, and two co-planar electrodes are strategically placed in relation to a microfluid channel to create a lens-free optical DEP cytometer. Lens-free optical cytometers have the advantage of simple optics, but have conventionally used 2-dimensional array detectors. In present invention, the cytometer is simplified by using a linear optical array containing detector pixels laid out in series in a singular row. Massively parallel analysis is possible as each detector pixel can be used to independently measure the velocity of a passing particle. With some optimization, more than one particle per second can be analyzed per detector. DEP particle analysis utilizes the velocity profile produced by Poiseuille flow, where the velocities of particles increase with distance from the DEP electrodes towards the center of the channel. The sign and magnitude of the dielectrophoresis response of each particle can thus be estimated from the sign and magnitude of velocity differences produced by DEP forces acting on the particles. Dielectrophoretic measurements of 10 μm beads and CHO cells have been taken with a prototype DEP cytometer produced in accordance with the presently illustrated embodiment. Using accompanying simulations for mapping, the method is capable of quantitative measurements of the dielectric response. Quantitative measurements of the Clausius-Mossotti factor for viable CHO cells from 100 kHz to 6 MHz were made, and are summarized herein further below in support of the utility of the present invention.

FIG. 1 shows the lens-free optical DEP cytometer of the preferred embodiment, which makes use of simple low cost components. A linear 256 photodiode array (AMS TSL1402R) was used as the optical detector, of which each pixel in the array measured 64 µm×56 µm, with an 8 µm space between pixels. As shown in the schematic diagram of the sensor in FIG. 1A, two blue LEDs (Wurth 150224BS73100 or QT-Brightek QBLP679E) were used to illuminate the fluid channel from above, and the detector is positioned beneath the channel. The LEDs were chosen for small emission area (400×400 µm) and were used without any aperture. The LEDs were held 100 mm above the channel. The components were assembled on an optical breadboard (Thorlabs MB4). A 50 µm deep, 18 mm wide channel was fabricated using double-sided adhesive tape (3M 9628FL) sandwiched between a pair of 1 mm×25 mm×75 mm glass slides, of which the bottom slide was equipped with patterned gold electrodes coated thereon. The front face of the optical detector array was positioned against the bottom of the electrode-equipped bottom glass slide. The two gold co-planar DEP electrodes, which measured 25 µm wide with a 25 µm gap between them in the prototype, were positioned such that the shadow of the particles would fall onto the optical detector array just after they have passed over the co-planar electrodes. The top glass slide featured an ultrasonically drilled 3 mm opening therethrough into channel space bounded on opposite sides and at one closed end by the double-sided tape, thereby creating a fluid intake port by which a sample fluid is admissible into the channel near said one closed end thereof. From here, the fluid can flow along the channel in a longitudinal direction thereof parallel to the elongated length dimension of the glass slides, i.e. the 75 mm slide length in the illustrated example.

A width direction of the channel lies perpendicularly transverse to the longitudinal direction thereof, thus corresponding to the 25 mm slide width in the illustrated example, and both the linear photodiode array and the electrodes lie parallel to this width direction of the channel, thus lying cross-wise to the channel in perpendicular relation to the longitudinal flow direction in which the fluid traverses the channel. The channel with the two cooperating DEP electrodes positioned above the detector array is shown in FIG. 1B, in which the optical detector array cannot be seen because the gold coating on the bottom glass sides covers most of the sensor's surface area. The positioning of the optical detector can more clearly be seen in FIG. 1C, in which the gold-coated bottom slide has been omitted for illustrative purpose.

Figure 2A:
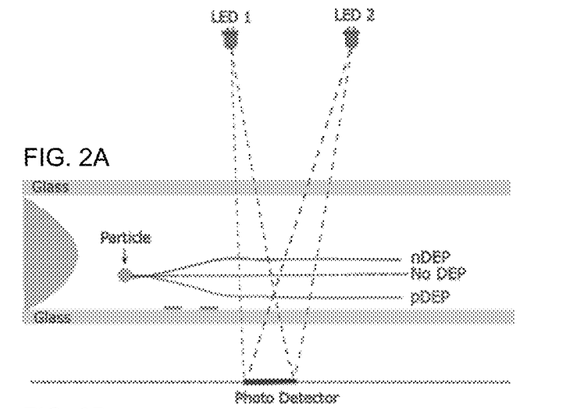
FIG. 2A shows a schematic side elevational view of the optical detector, microfluidic channel and trajectories of particles experiencing negative DEP (nDEP), no DEP and positive DEP (pDEP).

With reference the schematic view of FIG. 2A, in which the longitudinal fluid flow through the channel occurs in a left to right direction from the fluid intake port near the closed upstream end of the channel, both the electrodes and the optical detector reside downstream of the fluid intake, with the electrodes residing in close longitudinal proximity to the optical detector, but offset slightly upstream thereof in the longitudinal direction so that particles in the fluid pass by the optical detector after passing by the electrodes. With the electrodes residing in this upstream adjacency to the optical detector, particles are exposed to the electric field emitted by the electrodes, when energized, prior to passing by the optical detector.

Still referring to FIG. 2A, the LEDs and the optical detector are situated oppositely above and below the fluid channel so that the LEDs cast light onto the optical detector through the channel. While the illustrated embodiment has the LEDs disposed above the channel and the optical detector disposed below the channel so that the light is cast downwardly through the channel from the overlying LEDs to the underlying optical detector, this arrangement may be reversed so as to have the LEDs below the channel and the optical detector above the channel. The two LEDs are positioned to both cast light onto the optical detector, but are spaced from one another in the longitudinal direction of the channel so as to cast their light onto the optical detector at different angles of incidence. In the example shown in FIG. 2A in which the first LED resides upstream of the optical detector, but downstream of the electrodes so that the electrodes don't obstruct light from the first LED, while the second LED resides downstream from both the electrodes and the optical detector. The channel thus defines a longitudinal flow path through which the fluid, once having entered the channel through intake port at the upstream end of the channel, first passes by the electrodes, then passes between the first LED and the optical detector, and then between the second LED and the optical detector toward the downstream end of the channel.

The fluid is pushed through the channel using pressure-driven flow, which in testing of the prototype was produced by raising the altitude of the fluid reservoir above the channel by 3-6 cm. This produced a pressure of 3-6 mBar. Typically the pressure was adjusted to give an average particle velocity from 900 to 1500 µm/s. The LEDs were 100 mm above the channel, and the optical detector array was 2 mm below the channel. As a particle carried in the fluid passes between the detector and one of the LEDs, a shadow is cast on a pixel (i.e. single photodiode) of the array, and the output signal from that pixel decreases. Accordingly, passage of any given particle over any given pixel produces a pair of sequentially adjacent minima in the output signal that pixel, i.e. a first minimum resulting from the particle's obstruction of light between the first LED and the detector pixel, and a second minimum resulting from the particle's obstruction of light between the second LED and the detector pixel. Including the effects of refraction as the light passes through the glass slides, the shadows on the detector array are separated in space by a known distance, which in the tested prototype was 175 µm. By determining a time difference between the occurrence of the first and second minima, the known separation distance and time difference can be used to estimate the particle velocity. The parallel optical detecting array has the potential to detect the passage of many particles simultaneously, each at a respective pixel of the array, and each producing a respectively sequentially adjacent pair of minima in that pixel's output signal.

Figure 2B:
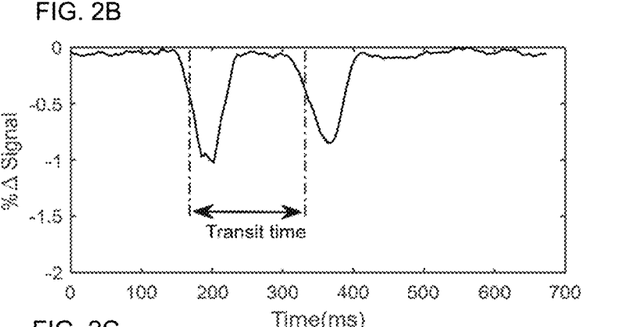
FIG. 2B shows a sample of a signal and transit time calculation using minima time.

FIG. 2A shows the schematic side view of the DEP cytometer with schematic trajectories for particles passing over the device. The output from one pixel of the photodetector, shown in FIG. 2B, is a series of electrical pulses, where the amplitude of each pulse is proportional to the optical power incident on a particular pixel. In the tested prototype, the clock sequences required to control the flow of signal pulses were provided by a microcontroller (PRC Teensy 3.6), and all 256 pixels could be digitized and logged every 4.5 ms, representing a rate could be maintained indefinitely. At an average velocity of 1300 µm/s, a particle would pass over a detector pixel of the prototype in 49 ms, meaning that each minimum would contain approximately 11 sample points. The time between signal minima due to the illumination from each LED would occur after the particle has travelled a distance of 175 µm. At a particle velocity of 1300 µm/s the time difference between minima ($\Delta t$) would be 135 ms and would contain approximately 30 sample points. Once the raw data was captured it was post processed to produce estimates of the particle arrival time and velocity.

Figure 2C:
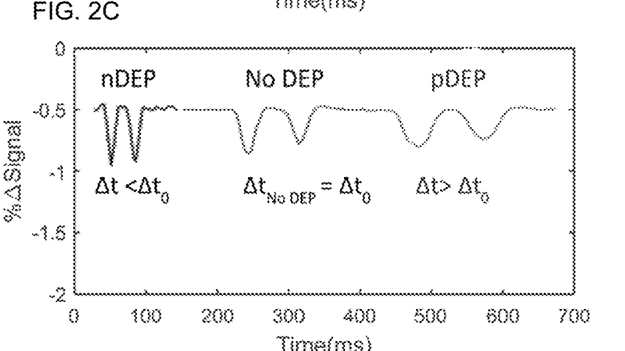
FIG. 2C shows detected signals for particles experiencing nDEP force ($\Delta t < \Delta t_0$), no DEP actuation ($\Delta t = \Delta t_0$), and pDEP force ($\Delta t > \Delta t_0$)

The dielectrophoretic (DEP) response of the particles is measured through a change in particle velocity. In the channel, there is a gradient in the velocity from the channel wall to the center of the channel produced by Poiseuille flow. When the particles enter the channel, gravity pulls the particles towards the bottom of the channel. The force of gravity is counteracted by the so-called lift force that increases as the particle approaches the bottom of the channel. The force of gravity is counteracted by the so-called lift force that increases as the particle approached the bottom of the channel [12]. These forces balance at some point and the particle will remain at this altitude unless some other force perturbs it. In the present system, DEP forces due to the co-planar electrodes produces attractive and repulsive forces that either push the particle above this equilibrium, or pull it below this equilibrium position. Due to the velocity gradient particles that are pushed up move into regions of higher velocity ($\Delta t < \Delta t_{No\ DEP}$), and particles that are pulled down move into regions of lower velocity ($\Delta t > \Delta t_{No\ DEP}$). FIG. 2C shows the corresponding signals recorded for particles experiencing nDEP ($\Delta t < \Delta t_{No\ DEP}$), no DEP ($\Delta t_{No\ DEP} = \Delta t_{No}$) and pDEP ($\Delta t < \Delta t_{No\ DEP}$) actuations. As described above, the optical detector array is positioned in close longitudinal adjacency to the electrodes to detect the particles just after flowing over the co-planar electrodes. Therefore, when the electrodes are energized, the optical detector array detects particles after they have been actuated by the DEP forces. The sign and magnitude of the velocity changes depend on the sign and magnitude of the DEP force [1,2].

In testing of the prototype, the particle velocity was estimated by post processing the raw sampled data using MATLAB. To reduce the noise the raw data was first filtered using a 5-point moving average filter. FIG. 2B shows one sample of signal after the moving average filter. Then the minima and their locations were determined using a minima detection function. Then a threshold of −0.3% was applied to identify minima of interest. In order to find the particle velocity, the time difference between two sequentially adjacent (i.e. consecutive) minima was used to calculate the reasons. Erroneous pairs of minima can occur due to peaks being above the threshold, having coincident particles and having multi-pixel shadows. These were partially eliminated by rejecting events with transit times less than 45 ms or greater than 437 ms. This corresponds to eliminating particles with velocities greater than 3880 μm/s and less than 400 μm/s. These steps yield a time and velocity for each valid particle.

Dielectrophoresis is the translation of a polarizable particle in a non-uniform electric field. The magnitude and direction of the DEP force depends on the effective polarizability of the particle with respect to its surrounding medium. For biological cells, this depends on the structure and electrical properties of its constituent components. Under the assumption of a spherical cell, the time averaged DEP force on the cells is given by [56]:

$$\vec{F}_{DEP} = 1.5 \tilde{\varepsilon}_m V_c \text{Re}\{K_{CM}\} \cdot \vec{\nabla} |E_{rms}^{DEP}|^2 \quad (1)$$

where $\tilde{\varepsilon}_m$ is the medium permittivity, $V_c$ is the cell volume, and $E_{rms}^{DEP}$ is the rms value of the electric field at the center of the cell. $\text{Re}\{K_{CM}\}$ is the real part of the Clausius-Mossotti factor expressed as:

$$K_{CM} = \frac{\tilde{\varepsilon}_p - \tilde{\varepsilon}_m}{\tilde{\varepsilon}_p + 2\tilde{\varepsilon}_m} \quad (2)$$

where, $\tilde{\varepsilon}_p$ and $\tilde{\varepsilon}_m$ are the complex permittivity of the cell and medium respectively, defined as $$\varepsilon = \varepsilon_0 \varepsilon_r + \frac{\sigma}{j\omega},$$

with ω being the frequency of the electric field.

Numerical simulations of the particle motion in the channel with dielectrophoretic forces were compared to the experimental observations. In order to simulate the particle trajectory in the channel, fluid dynamics simulation is employed. Here, the movement of particles with various dielectric constants, and hence $\text{Re}\{K_{CM}\}$, was simulated using COMSOL Multiphysics, which includes the presence of gravity, buoyancy, lift, and drag forces in addition to the DEP force [12]. The $\text{Re}\{K_{CM}\}$ constant used for the PSS was −0.5 and the $\text{Re}\{K_{CM}\}$ constants for the cells were taken from [12]. Fluid flow in a microfluidic channel can be assumed laminar and the fluid velocity at any altitude, h, from the bottom of the channel is given by $$v_m = 6\langle v_m \rangle \left(\frac{h}{H}\right)\left(1 - \frac{h}{H}\right) \quad (3)$$

where $\langle v_m \rangle$ is the average velocity of the particle in the channel, h is the distance from the center to the bottom of the channel, H is the height of the channel. The majority of cells flowing in the microfluidic channel are at an equilibrium altitude before entering the DEP actuation region. The equilibrium altitude, $h_{eq}$, of a cell is the elevation at which gravity, buoyancy, and lift forces are in balance. The following cubic polynomial in h solves for the equilibrium height:

$$h^3 - (H+R)h^2 + (H \cdot R)h + \frac{\gamma v H^2}{2} = 0 \quad (4)$$

where $\gamma = 9C\eta/(2\pi g H \Delta \rho)$, v is the entrance velocity obtained by measurements, R is the particle radius, C=0.031 is the lift coefficient, η=0.001 is the viscosity of the medium, g=9.81 m/s² is the gravitational acceleration, and Δρ=0.05 is the difference in densities of the cell and suspension medium. This formula gives three roots: two are positive and one is negative (non-physical). The only valid root is below mid-channel, $h_{eq}$, which is the value we choose [57].

The starting point of the particle trajectory simulation is determining the equilibrium height of a particle. Considering cells at their equilibrium height while entering the DEP region, the experimentally obtained velocity, $V_1$, corresponds to the particle's velocity at its equilibrium height, Employing equation (4) and obtained $V_1$, equilibrium height can be determined. Then applying equation (3), the average velocity of the particle in the channel is determined. With the particle entering at a given height, $h_1$, and subjected to DEP and hydrodynamic forces, we obtain its exit altitude, $h_2$, at the location of the optical sensing region, for different values of $\text{Re}\{K_{CM}\}$. The exit velocity corresponds to the obtained exit height can be calculated using equation (3).

The details of the cell growth and preparation are covered in detail elsewhere, but are briefly outlined here [19]. Chinese hamster ovary cells (CHODG44-EG2-hFc/clone 1A7), provided by Yves Durocher of the National Research Council, were grown in 250 ml shaker flasks and incubated at 37° C. with a 10% $CO_2$ overlay on a shaker platform (120 rpm). The cells were passaged every 2-3 days with a seeding density of $2\times10^5$ cells/ml in BioGro-CHO serum-free medium (BioGro Technologies, Winnipeg, MB) supplemented with 0.5 g/l yeast extract (BD, Sparks, Md.), 1 mM glutamine (Sigma, St. Louis, Mo.), and 4 mM GlutaMax I (Invitrogen, Grand Island, N.Y.). Samples for DEP measurement were prepared by centrifuging and resuspending day 2 cells in a mix of BioGro CHO medium and low conductivity medium [22.9 mM sucrose (Sigma), 16 mM glucose (Fisher), 1 mM $CaCl_2$) (Fisher), 16 mM Na2HPO4 (Fisher)] with 1:15 ratio. A 16 mL sample was obtained with a concentration of $2\times10^5$ cells/ml, osmotic pressure 291 mOsm/kg and conductivity 0.17 S/m.

Signals obtained for ten µm diameter PSS flowing through the cytometer are shown in FIG. 2B. When the PSS passes over the detector it refracts the light causing a decrease in the optical power incident on the detector. For the 10 µm PSS using two LEDs, a decrease in the optical power of 1.2% is typically observed. The noise in the digitized signal is ~0.026% RMS. The two minima are not equal amplitude due to the illumination from each LED being mismatched. This is due to the optical emission being different, and differences in the loss in along the optical path due to effects such as dust. The velocity of the particle is calculated from the time difference between minima estimated using the methods outlined above. When DEP potentials are applied to the co-planar electrodes the particles are actuated and the velocity perturbed depending on the sign of the DEP forces. In FIG. 2C examples are shown of particles with negative DEP forces (nDEP), no DEP and positive DEP forces (pDEP). In the case of nDEP the particle velocity increases, leading to a decrease in the time difference between minima. For pDEP the particle velocity decreases, and the time between minima increases.

Figure 3A:
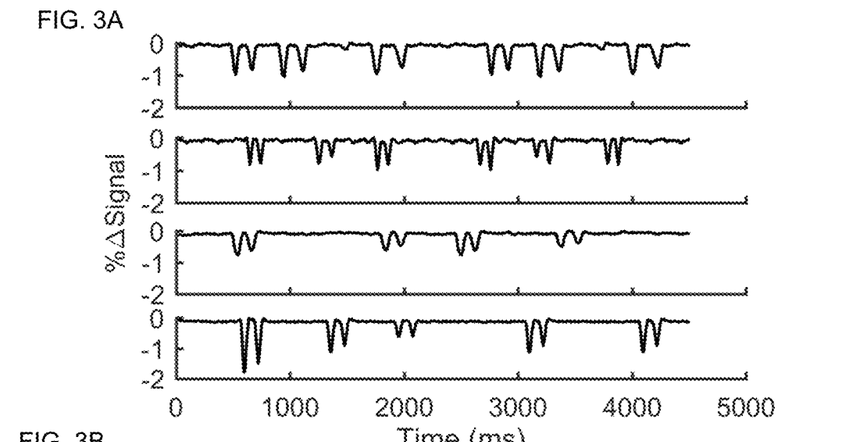
FIG. 3A shows example signals from four pixels for a 4.5-second time period.
Figure 3B:
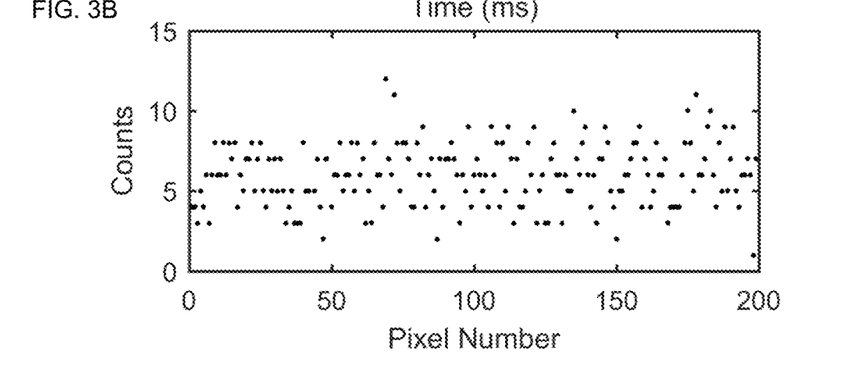
FIG. 3B shows the particle count for each pixel in 4.5 seconds; from which overall system throughput was found to be 263 particles per second.

The possible throughput of the approach was tested using PSS beads. The particle density was chosen to produce a condition where there is relatively small probability of multiple particles being present in the analysis region at the same time. Typical signals from several pixels for a 4.5 second time period are shown in FIG. 3A. It is not possible to show results from all pixels. In this instance, 200 pixels are being sampled corresponding to 12.8 mm of channel width. The particles have an average velocity of 1500 µm/s. In a 4.5 second period 1185 particles are detected, corresponding to an average rate of 1.2 particles/s for each pixel. Given the average velocity of the particles, the average space between each particle is 1; 250 µm. Given the 175 µm spacing between LED shadows, this will produce a condition with low probability of 2 particles being in the analysis region at the same time. The particle distribution is also reasonably uniform for each pixel. The particle count for each pixel is shown in FIG. 3B.

The shadows for each particle are largely confined to one pixel. There is a small 8 µm gap between each pixel and the fraction of particles producing shadows on more than one pixel is less than 4.5%. To a large degree each pixel can be regarded as producing a signal that is independent of the particles passing over any other pixel. Therefore, with the configuration presented up to 256 pixels are possible, that can each be used to simultaneously analyze particles. This has been tested by using particle concentrations that approach this limit. Under these conditions, particle analyses rates of 330 particles/s have been reached. This corresponds to a rate of 19,800 per minute.

The approach employed in the initial prototype work is highly scalable. Optical sensors of the type used are available in arrays reaching 3300 pixels (400 pixels per inch over 8.5 inches) for applications such as document scanners. The channels and electrode arrays could also be scaled to these dimensions. The required computation can also be modularized and therefore systems reaching 250,000 particles per minute are achievable. Further, the very large channels used are not prone to clogging and can be operated for long periods of time.

Figure 4A:
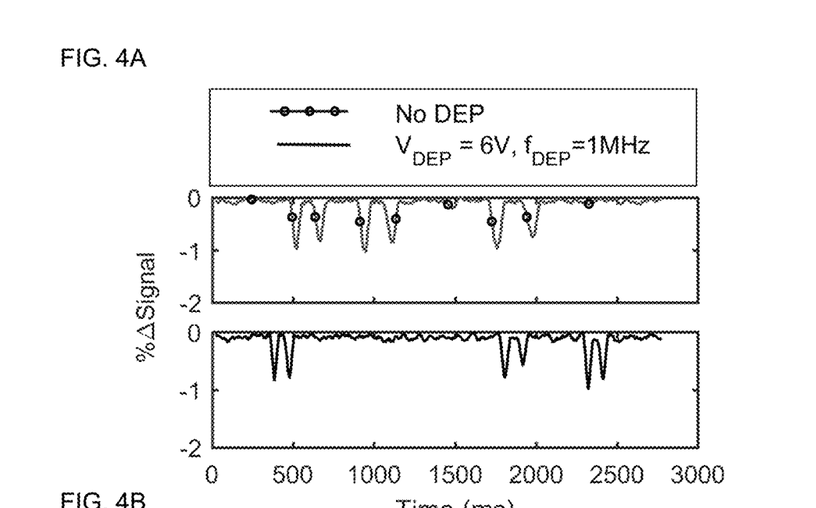
FIG. 4A shows an example of signal traces for 10 μm polystyrene spheres (PSS) before and after applying DEP force.
Figure 4B:
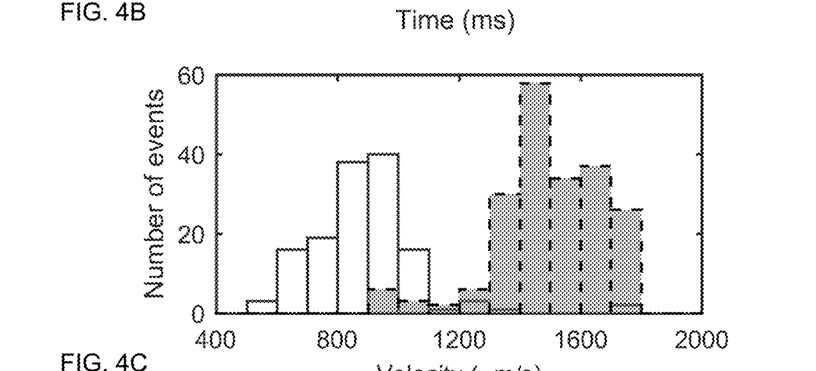
FIG. 4B shows histograms of the PSS before applying DEP and after applying 8 Vpp with 1 MHz frequency to the electrodes.
Figure 4C:
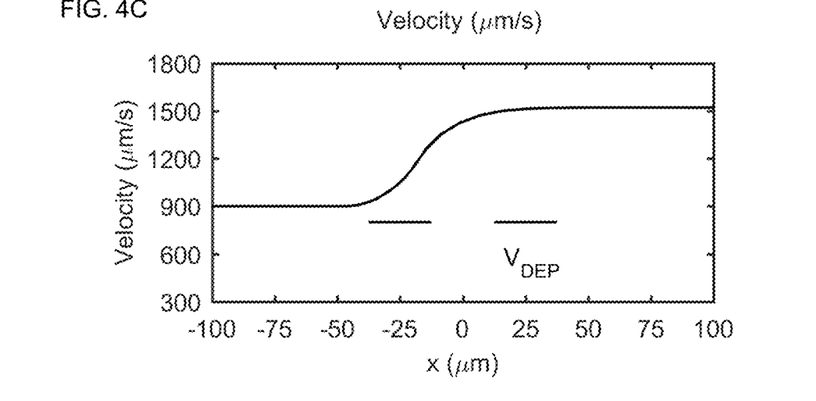
FIG. 4C shows particle velocity simulations in the channel for PSS with −0.5 Clausius-Mossotti factor ($K_{CM}$).

FIG. 4A shows the example PSS signals before and after applying DEP. When a 6V peak to peak voltage at 1 MHz is applied to the co-planar electrodes nDEP forces are experienced by PSS particles and the particles are actuated into regions of higher velocity. The effect of the DEP forces can be seen in signal traces where the minima spacing is clearly shorter, after the DEP potentials are applied. In the histograms shown in FIG. 4B the 10 µm PSS particles have a mean velocity of 900 µm/s before the application of the DEP signals (unshaded bins). After the application of the DEP forces the mean velocity is 1500 µm/s (shaded bins). This can be compared to particle trajectory simulations FIG. 4C where the simulation is adjusted to first yield an equilibrium position 8.9 µm above the channel bottom and a velocity of 900 µm/s. After passing the co-planar electrodes with DEP actuation applied the particles rise to 22.2 µm above the bottom of the channel and to a velocity of 1518 µm/s.

Figure 5A:
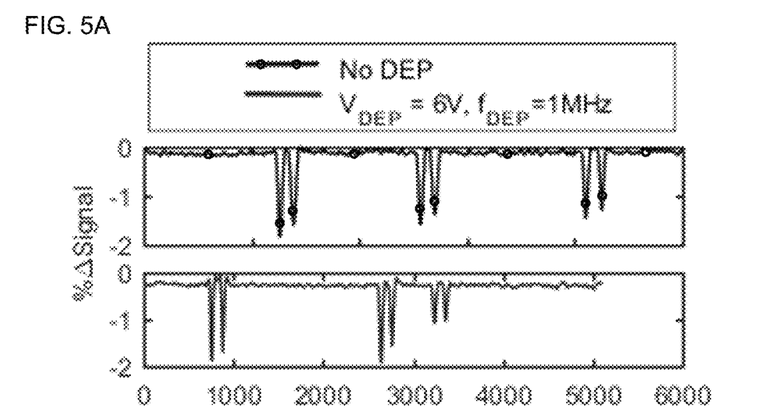
FIG. 5A shows AN example of signal traces for Chinese hamster ovary (CHO) cells before and after applying DEP force.
Figure 5B:
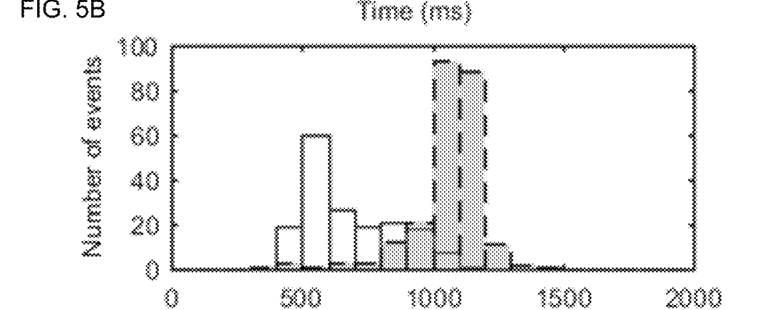
FIG. 5B shows histograms of the cells before applying DEP and after applying 10 Vpp voltage with 6 MHz frequency to the electrodes.
Figure 5C:
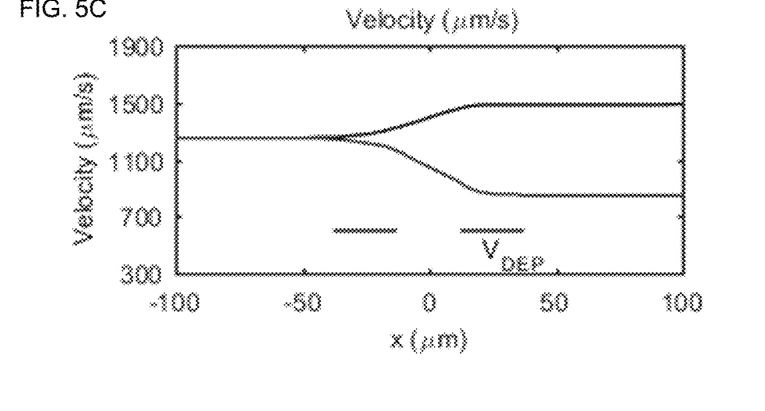
FIG. 5C shows CHO cells velocity simulations in the channel for −0.32 and 0.32 Clausius-Mossotti factor.

FIG. 5A shows the example of CHO cell signals before and after applying DEP. When a 10V peak to peak at 6 MHz voltage is applied to the co-planar electrodes pDEP forces are experienced by CHO cells and the cells are actuated into regions of lower velocity. The effect of the DEP forces can be seen in signal traces where the minima spacing is clearly longer, after the DEP potentials are applied. In the histogram shown in FIG. 5B the CHO cells have a mean velocity of 1250 µm/s before the application of the DEP signals (shaded bins). After the application of the DEP forces the mean velocity is 600 µm/s (unshaded bins). This can be compared to particle trajectory simulations FIG. 5C where the simulation is adjusted to first yield an equilibrium position 13.2 µm above the channel bottom and a velocity of 1250 µm/s. After passing the co-planar electrodes with DEP actuation applied the particles drop to 8 µm above the bottom of the channel and to a velocity of 850 µm/s.

Figure 6A:
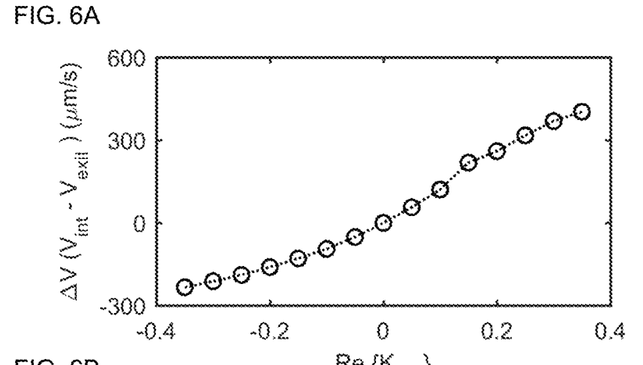
FIG. 6A shows simulation results of the change in velocity of the CHO cells for different values of the Clausius-Mossotti factor in −0.35 to 0.35 range.
Figure 6B:
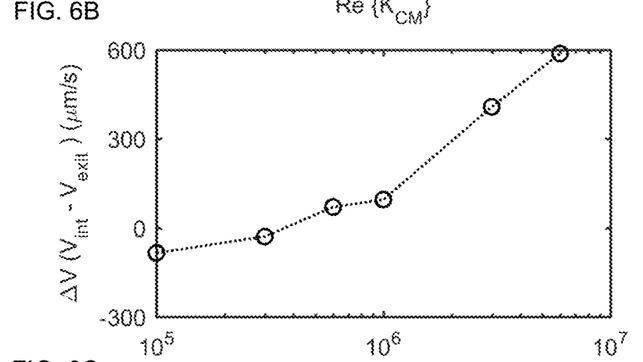
FIG. 6B shows experimental results of CHO cells velocity changes with the field applied for 15-30 seconds to the DEP electrodes.
Figure 6C:
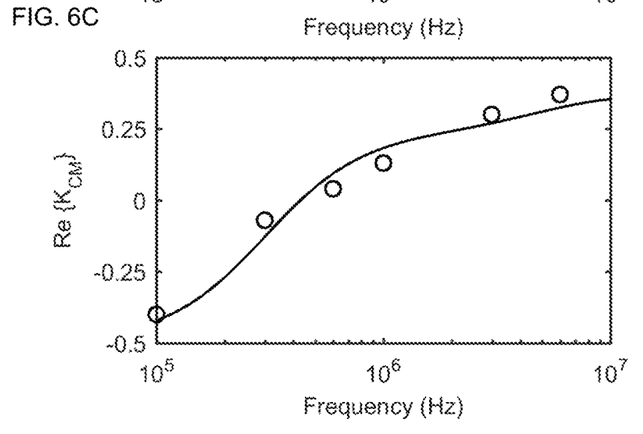
FIG. 6C shows theoretical estimates (solid lines) of the $K_{CM}$ for CHO cells with the parameters obtained from elsewhere [12], and experimental results of the $K_{CM}$ (circled points) mapped to Clausius-Mossotti factor using simulation an experimental results in (a, b).

This analysis method also can produce estimates of the dielectric properties of the particles versus frequency. Using particle trajectory simulations a mapping between velocity differences before and after application of the DEP forces and Clausius Mossotti Factor ($K_{CM}$) was determined for $K_{CM}$ from −0.35 to +0.35. This mapping is shown for CHO cells in FIG. 6A. At 100 kHz the cells experience nDEP with a $K_{CM'}$ of −0.25 and the velocity change is negative. At 6 MHz the cells experience pDEP with a $K_{CM}$ of +0.32 the velocity change is positive. The curve is not symmetric about a $K_{CM}$ of 0, as the DEP forces decrease with distance from the electrodes and therefore the magnitude of velocity changes produced by nDEP forces is lower. The velocity change was experimentally determined by measuring the velocity of CHO cells prepared as described above for a deenergized-measurement period of approximately 15-30 seconds with no electric field applied, and comparing this with the velocity measured with the electric field applied at the DEP electrodes in an energized-measurement period of 15-30 seconds. These velocity measurements are shown in FIG. 6B. The results of FIG. 6B can be mapped to $K_{CM}$ using FIG. 6A and these are shown in FIG. 6C along with the theoretical estimate of the $K_{CM}$ for CHO cells [12]. The experimental estimate for the $K_{CM}$ and the theoretical estimate are within 0.058. Being able to detect changes in $K_{CM}$ of 0.058 is useful as biological changes such as apoptosis produces a change of 0.4 in the $K_{CM}$ at 6 MHz [19].

In summary, a lens-free dielectrophoresis (DEP) cytometer for analysis of single biological cells can be created using two light emitting diodes (LEDs), a co-planar electrode, and a linear optical detector array. As a particle passes over a pixel of the detector array, two minima are produced in the output signal from that pixel, each minimum being attributed to obstruction of light from a respective one of the LEDs. The particle velocity can be estimated from the time difference between the minima, as the distance between the two physical points at which the light obstruction occurs is known. Each pixel of the detector can independently measure the velocity of a passing particle and hence a wide channel (e.g. ~15 mm) can be employed to carry many particles simultaneously particles. The wide channel greatly reduces the probability of clogging. Especially in the instance of a wide channel, this method is capable of significant particle analysis rates, for example exceeding 300 per second in the forgoing wide channel example. In addition, the method has the potential to quantitatively measure dielectric response. The Clausius-Mossotti factor from 100 kHz to 6 MHz was measured for viable CHO cells and was within 0.058 of the expected values. The system is composed of simple modular components and with modest optimization, a throughput of thousands of particles per second should be achievable.

While the illustrated embodiment, based on the initial prototype, employs glass slides as top and bottom members of the channel, and double sided tape to delimit side and end boundaries of the channel, alternative materials and constructions may be employed, provided that the selected material(s) of the top and bottom members of the channel are sufficiently transparent to enable transmission of light through the channel from top to bottom, or vice versa, between the light emitters and the optical detector array. Likewise, while use of a gold coated slide to define both a channel member and the co-planar electrodes is convenient, the selection of conductive material for the electrodes need not be limited to gold specifically, nor is the particular use of a conductive coating on the channel member the sole option for mounting the electrodes in suitably relation to the channel.

Since various modifications can be made in my invention as herein above described, and many apparently widely different embodiments of same made, it is intended that all matter contained in the accompanying specification shall be interpreted as illustrative only and not in a limiting sense.

The invention claimed is:

1. A lens-free dielectrophoretic cytometer comprising:
a fluid channel;
an inlet port arranged for admission of fluid into said fluid channel for flow therethrough in a longitudinal direction thereof;
a linear photodiode array lying cross-wise to said fluid channel in the width direction thereof at a spaced distance downstream from the inlet port;
situated oppositely above and below the fluid channel:
a pair of cooperating electrodes also lying cross-wise to said fluid channel in the width direction thereof at a location situated downstream from the inlet port, and in upstream adjacency to the photodiode array; and
a pair of light emitters positioned in longitudinally spaced apart relation from one another to cast light onto the photodiode array at different angles of incidence.

2. The cytometer of claim 1 further comprising circuitry coupled to the photodiode array, including processing circuitry configured to detect pairs of sequentially adjacent minima in output signals from each individual pixel of the photodiode array, and to determine and record a time difference between occurrence of first and second minima in each said pair of sequentially adjacent minima.

3. The cytometer of claim 2 wherein said processing circuitry is configured to detect said pairs of sequentially adjacent minima and determine and record said time difference during both a deenergized state of said electrodes and at least one energized state of said electrodes.

4. The cytometer of claim 3 wherein said circuitry includes control circuitry configured to control switching of the electrodes between said deenergized and energized states.

5. The cytometer of claim 2 wherein said processing circuitry is configured to calculate particle velocities using the time differences from the pairs of sequentially adjacent minima.

6. The cytometer of claim 1 wherein the fluid channel is delimited between transparent top and bottom members through which light from the light emitters is transmittable to the photodiode array.

7. The cytometer of claim 6 wherein the electrodes comprise strips of conductive material coated on one of said transparent top and bottom members.

8. The cytometer of claim 6 wherein said transparent top and bottom members comprise glass.

9. The cytometer of claim 1 wherein said pair of light emitters comprise a pair of light emitting diodes.

10. A method of performing dielectrophoretic cytometry, said method comprising:
(a) causing flow of a fluid sample on a flow path that passes between (i) a linear photodiode array that lies cross-wise to said flow path, and (ii) a pair of light emitters that are spaced apart along said flow path to cast light on said linear photodiode array at different angles of incidence; and
(b) during the flow of said fluid sample along said flow path, and during both a deenergized-measurement period characterized by absence of any applied electric field to the flowing fluid, and an energized-measurement period characterized by application of an electric field to the flowing fluid, detecting from each pixel of the photodiode array pairs of sequentially adjacent minima in an output signal of said pixel, wherein each detected pair of sequentially adjacent minima comprises a first minimum denoting passage of a particle between said pixel of the photodiode array and a first one of the light emitters, and a second minimum denoting passage of said particle between the said pixel of the photodiode array and a second one of the light emitters.

11. The method of claim 10 comprising determining and recording a time difference between occurrence of the first and second minima in said each detected pair of sequentially adjacent minima.

12. The method of claim 11 comprising calculating particle velocities based on the time differences from the pairs of sequentially adjacent minima.

13. The method of claim 10 comprising determining and recording a time difference between occurrence of the first and second minima in said each detected pair of sequentially adjacent minima, calculating particle velocities using the time differences from the pairs of sequentially adjacent minima, and comparing the particle velocities from the energized and deenergized measurement periods to characterize particles found in the sample fluid.

14. The method of claim 10 wherein the method is performed with an apparatus that comprises:
- a fluid channel;
- an inlet port arranged for admission of fluid into said fluid channel for flow therethrough in a longitudinal direction thereof;
- a linear photodiode array lying cross-wise to said fluid channel in the width direction thereof at a spaced distance downstream from the inlet port;
- situated oppositely above and below the fluid channel:
  - a pair of cooperating electrodes also lying cross-wise to said fluid channel in the width direction thereof at a location situated downstream from the inlet port, and in upstream adjacency to the photodiode array; and
  - a pair of light emitters positioned in longitudinally spaced apart relation from one another to cast light onto the photodiode array at different angles of incidence.

* * * * *